United States Patent
Tseng et al.

(10) Patent No.: US 11,369,268 B2
(45) Date of Patent: Jun. 28, 2022

(54) BRAIN-FUNCTION IMAGE DATA AUGMENTATION METHOD

(71) Applicant: Institute of Nuclear Energy Research, Atomic Energy Council, Executive Yuan, R.O.C, Taoyuan (TW)

(72) Inventors: Fan-Pin Tseng, Taoyuan (TW); Yu-Ching Ni, Taoyuan (TW); Wen-Bin Lin, Taoyuan (TW)

(73) Assignee: INSTITUTE OF NUCLEAR ENERGY RESEARCH, ATOMIC ENERGY COUNCIL, EXECUTIVE YUAN, R.O.C, Taoyuan (TW)

( * ) Notice: Subject to any disclaimer, the term of this patent is extended or adjusted under 35 U.S.C. 154(b) by 252 days.

(21) Appl. No.: 16/885,478

(22) Filed: May 28, 2020

(65) Prior Publication Data

US 2020/0375462 A1 Dec. 3, 2020

(30) Foreign Application Priority Data

May 31, 2019 (TW) ................................ 108118900

(51) Int. Cl.
*A61B 5/00* (2006.01)
*G06T 7/00* (2017.01)

(52) U.S. Cl.
CPC .......... *A61B 5/0042* (2013.01); *A61B 5/4064* (2013.01); *A61B 5/4088* (2013.01); *G06T 7/0012* (2013.01); *G06T 2207/10108* (2013.01)

(58) Field of Classification Search
CPC ... A61B 5/0042; A61B 5/4064; A61B 5/4088; A61B 6/037; A61B 6/501; A61B 6/5211;
(Continued)

(56) References Cited

U.S. PATENT DOCUMENTS

| 7,729,749 B2 * | 6/2010 | Roessler | A61B 5/0059 600/476 |
| 2006/0292547 A1 * | 12/2006 | Pettegrew | A61K 36/28 435/4 |

OTHER PUBLICATIONS

Liu, Mengyuan "Patch-based augmentation of Expectation-Maximization for brain MRI tissue segmentation at arbitrary age after premature birth" NeuroImage 127. (Year: 2016).*

* cited by examiner

Primary Examiner — Emily C Terrell
Assistant Examiner — Molly Wilburn
(74) Attorney, Agent, or Firm — Locke Lord LLP; Tim Tingkang Xia, Esq.

(57) ABSTRACT

A brain-function image data augmentation method includes: a step of providing a target database including a plurality of image-data information; a step of, based on a plurality of image-data expected information in an expectation-value database, calculating a ratio of the plurality of image-data expected information with respect to different ages; a step of, based on the plurality of image-data information and the ratio, obtaining image-data ratio information with respect to an estimated age; a step of establishing a relationship for each pair of the image-data information and the image-data expected information; a step of, based on the relationship, the ratio and the image-data information, calculating an estimated image-data information with respect to the estimated age; and, a step of combining linearly the estimated image-data information and the image-data ratio information so as to generate an augmented image-data information with respect to the estimated age.

6 Claims, 1 Drawing Sheet

(58) Field of Classification Search
CPC ......... G06T 7/0012; G06T 2207/10108; G06T 11/00
See application file for complete search history.

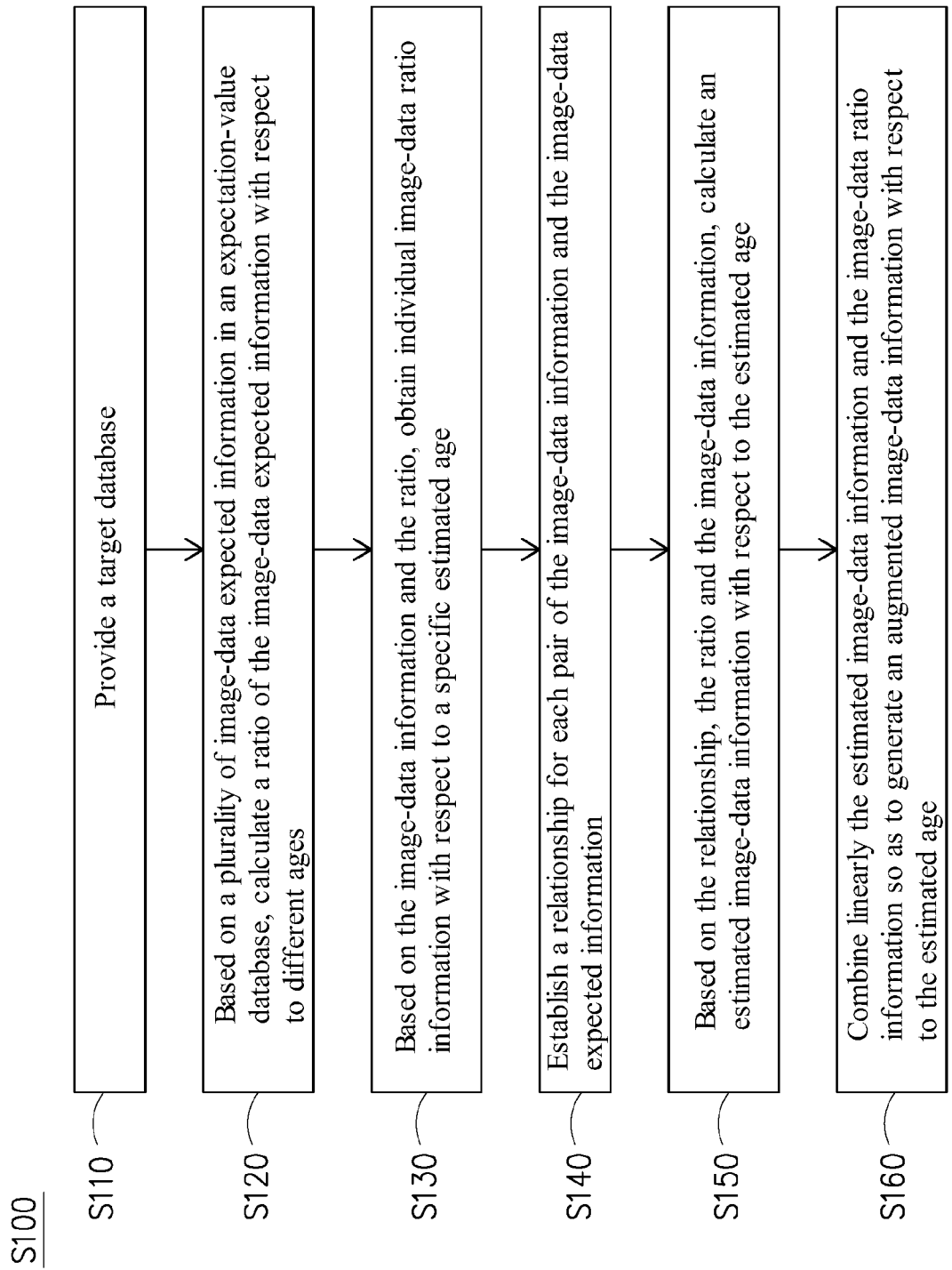

BRAIN-FUNCTION IMAGE DATA AUGMENTATION METHOD

CROSS REFERENCE TO RELATED APPLICATION

This application claims the benefits of Taiwan application Serial No. 108118900, filed on May 31, 2019, the disclosures of which are incorporated by references herein in its entirety.

TECHNICAL FIELD

The present disclosure relates in general to a brain-function image data augmentation method.

BACKGROUND

Dementia is well known to be one of neurodegenerative diseases, yearly population of this disease is increased with the coming era of super-aged society. Currently, confirmation of the dementia requires necessary investigation procedures upon various evidences obtained from versatile testing. In particular, the nuclear medicine head/brain SPECT examination is one of important credible methods for clinical determining the dementia, recommended by most of international medical centers and societies. By having the Alzheimer's disease (AD) as a typical example of the dementia, a regular diagnosis for measuring this dementia is mainly performed by questionnaires, and then the nuclear medical cerebral blood perfusion examination such as the Tc-99m-ECD brain SPECT would be further introduced for image diagnosis. In addition, a sympathetic examination such as the I-123-MIBG chest scan can be performed for further confirming the dementia with Lewy bodies (DLB). Thereupon, potential patients can receive relevant follow-up medication.

In comparison with most of advanced countries, domestic count for nuclear medical examinations is relatively low. Two major reasons are concluded as follows after massive clinical consultation. Firstly, it is well known that the image interpretation can be only provided subjectively by the nuclear medicine physician. However, due to complicity in the brain structure, individual differences, and lack of clinical experience and reference brain images, thus, most of physicians other than the nuclear medicine physicians, it is already stereotype that judgments made upon the nuclear medical images are too subjective, with low reproducibility, false positivity or negativity. Thus, those nuclear medical judgments are not sufficiently relied on by the forefront neurosurgery or dementia physicians. Secondly, cross-hospital or cross-instrument differences make the image judgments further unconvincing. Other problems that may also cause incredibility to current nuclear medical imaging include: incoherent quality in nuclear medical imaging for dementia, failure to perform regular maintenance upon equipment for nuclear medical imaging examinations, lack of standard procedures for performing brain examinations, in-feasibility for providing standardized clinical images and so on. All or any of the aforesaid reasons would lead to a possibility that the same disease on the same patient may be differently diagnosed from differences of the imaging.

Recently, as the technology of deep learning grows rapidly, plenty of tagged data and multi-layer neural network architectures are introduced to perform computer-simulated training so as to effectively process classification and expectation upon images, letters and/or voices. In comparison with professional judgments, the computer simulation can even provide more precise diagnosis. However, the aforesaid computer technique is basically relied on a data-driven algorithm that requires a database having a huge number of image data.

In a typical conventional method, labors are largely devoted to collect nuclear medical images. Since the nuclear medical images are hard to be collected and the collected number is usually limited to usable labors. In a normal hospital, the standard operating procedures (SOP) are firstly to evaluate by a questioning method or a questionnaire scale, and then to determine whether or not nuclear medical imaging is necessary. Thereupon, sufficient nuclear-medicine brain-function image data are not easy to be collected, especially those for health people. Generally speaking, in a training session of deep learning, a technique of data augmentation is usually used to magnify the number of training samples, and to improve possible data imbalance. In training the imaging, actions such as rotations, displacements, scaling, turning and/or inclinations are usually required. It is understood that the aforesaid rigid body motions are massively applicable to daily photo editing, such as magnifying or turning over a cat (where the cat is still a cat after the rigid body motions). However, these rigid body motions are not suitable to perform augmentation upon the nuclear-medicine brain-function image data. Mostly, if the rigid body motions are applied to this field of imaging, some physiological characteristics would be lost.

Hence, an improved brain-function image data augmentation method to resolve the aforesaid concerns is definitely urgent to the skill in the art.

SUMMARY

An object of the present disclosure is to provide a brain-function image data augmentation method for augmenting nuclear-medicine brain-function image data so as to compensate possible data shortages. Thus, for example, while a single photon emission computed tomography (SPECT) performs specific algorithms such as machine learning and Z-score (Standard score), and meets a data shortage in healthy people, it would be highly possible that the related statistic variance would not be ignored. In this situation, the brain-function image data augmentation method provided in this disclosure can be introduced to improve data imbalance occurring in the training of deep learning.

In this disclosure, the brain-function image data augmentation method includes: a step (a) of providing a target database including a plurality of image-data information, wherein the image-data information being the at least one nuclear-medicine brain-function image data with respect to the different ages; a step (b) of, based on a plurality of image-data expected information in an expectation-value database, calculating a ratio of the plurality of image-data expected information with respect to different ages; a step (c) of, based on the plurality of image-data information and the ratio, obtaining image-data ratio information with respect to an estimated age; a step (d) of establishing a relationship for each pair of the image-data information and the image-data expected information; a step (e) of, based on the relationship, the ratio and the image-data information, calculating an estimated image-data information with respect to the estimated age; and, a step (f) of combining linearly the estimated image-data information and the image-data ratio information so as to generate an augmented image-data information with respect to the estimated age.

In one embodiment of this disclosure, the step (f) includes a step (f1) of, based on a first weighting value and a second weighting value to linearly combine the estimated image-data information and the image-data ratio information, and a step (f2) of adjusting the first weighting value and the second weighting value to generate different augmented image-data information.

In one embodiment of this disclosure, the step (b) includes a step of providing the expectation-value database, the expectation-value database including the plurality of image-data expected information, each of the plurality of image-data expected information being a mean expected image data with respect to the different ages, the mean expected image data being a voxel value greater than zero.

In one embodiment of this disclosure, the step (d) includes a step (d1) of averaging voxel values of the plurality of image-data information to obtain an averaged image-data information, and a step (d2) of, based on a linear regression model, establishing the relationship between the averaged image-data information and the plurality of image-data expected information with respect to the estimated age.

In one embodiment of this disclosure, the step (a) includes a step of capturing at least one nuclear-medicine brain-function image data for different ages.

In one embodiment of this disclosure, the step (e) includes a step (e1) of, based on the relationship, obtaining an approximate image-data expected information by plugging each of the image-data information into the relationship, a step (e2) of, based on the ratio and the approximate image-data expected information, obtaining an estimated image-data expected information with respect to the estimated age, and a step (e3) of, based on the relationship and the estimated image-data expected information, obtaining the estimated image-data information.

As stated, in the brain-function image data augmentation method provided by this disclosure, the expectation-value database having given image-data expected information is introduced to expand the training data set of the deep learning.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein:

FIG. 1 is a schematic view of an embodiment of the brain-function image data augmentation method in accordance with this disclosure.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Referring now to FIG. 1, an embodiment of the brain-function image data augmentation method in accordance with this disclosure is schematically shown. In thus embodiment, the brain-function image data augmentation method S100 can be performed by hardware (such as a controller or an IC), software (such as program commands performed by the controller), or a combination of hardware and software. For example, a controller can be connected with a target database and an expectation-value database so as to have the program commands for the controller to perform the brain-function image data augmentation method S100 of this disclosure.

It shall be explained that, while in performing the brain-function image data augmentation method S100, following steps can be included. Firstly, a standard normalization process shall be performed. To overcome inconsistency of nuclear medical images from different hospitals and different instruments, the standard normalization process shall be performed. For example, through a statistical parametric mapping (SPM) of a specific software program to perform normalization to perform normalization, or through prosthesis experiments to perform calibration, the concerned inconsistency across brands of instruments and hospitals can be resolved. Then, digital normalization is executed on the images. For example, an image mask can be firstly introduced to erase background noises of the brain-function image, then an appropriate blurring function is applied to have the image convoluted, and finally an average value can be obtained by dividing overall voxels of the entire image by all non-zero voxels.

In this disclosure, the brain-function image data augmentation method S100 includes the following Step S110 to Step S160. In performing Step S110, a target database is provided, in which the target database includes a plurality of image-data information. In one embodiment of this disclosure, a plurality of or at least one nuclear-medicine brain-function image data for different ages is captured. Herein, $f_t(x)$ stands for the image-data information, in which f stands for the target database, x stands for all non-zero voxel positions, and t stands for a specific age or an age range. In this embodiment, the image-data information is at least one nuclear-medicine brain-function image data with respect to individual ages. For example, $f_{76}(x)$ stands for the nuclear-medicine brain-function image data with respect to a 76-year-old testee, or $f_{74}(x)$ stands for the nuclear-medicine brain-function image data with respect to a 74-year-old testee.

Then, in performing Step S120, based on a plurality of image-data expected information in an expectation-value database, calculate a ratio of the image-data expected information with respect to different ages. In detail, following steps are included. Firstly, the expectation-value database is provided, in which the expectation-value database includes a plurality of image-data expected information. In one embodiment of this disclosure, $g_t(x)$ stands for the image-data expected information, in which g stands for the expectation-value database, x stands for all non-zero voxel positions, and t stands for a specific age or aging range. Each of the image-data expected information, as known information, is a mean expected image data with respect to a corresponding age or aging range, and the mean expected image data is a voxel value greater than zero. For example, $g_{76\sim85}(x)$ stands for the mean expected image data with respect to the aging range from 76~85 years old.

In one embodiment of this disclosure, while in managing the expectation-value database, the t value is dependent on the number of the image-data information $f_t(x)$, and an interpolation manipulation is applied to obtain the $g_t(x)$ with respect to the t. For example, if the current expectation-value database includes expectation values for the aging ranges of 55~64, 65~74 and 75~84, then the image-data information would be seen as $g_{55~64}(x)$, $g_{65~74}(x)$ and $g_{75~84}(x)$, and $g_{60}(x)$, $g_{61}(x)$, $g_{79}(x)$, $g_{60~61}(x)$, $g_{62~63}(x)$ and so on can be obtained through interpolations. In addition, a ratio between any two image-data expected information with respect to different ages or aging ranges can be calculated. For example, different ages or aging ranges t can be used to calculate a ratio $r_{t/t'}(x)$ of the $g_t(x)$ at each voxel x for different ages or aging ranges t, i.e., $r_{t/t'}(x)=g_t(x)/g_{t'}(x)$. For example, $r_{74/70}(x)=g_{74}(x)/g_{70}(x)$.

Then, in performing Step S130, based on each of the image-data information and each of the ratios, individual image-data ratio information with respect to a specific estimated age or aging range can be obtained. For example, f-ratio$_t(x)$ stands for the image-data ratio information to be derived by dividing $f_t(x)$ by $r_{t/t'}(x)$. Namely, f-ratio$_{t'}(x)=f_t(x)/r_{t/t'}(x)$. For example, with the $f_{74}(x)$ in the target database, i.e., the nuclear-medicine brain-function image data for the age of 74, then if the nuclear-medicine brain-function image data for the age of 70 is wanted from the $f_{74}(x)$, it can be obtained by f-ratio$_{70}(x)=f_{74}(x)/r_{74/70}(x)$.

Then, in performing Step S140, a relationship for each pair of the image-data information and the image-data expected information can be established by the following calculations. The calculations include the steps of: averaging voxel values of the image-data information so as to obtain an averaged image-data information, then evaluating a machine learning algorithm to obtain the relationship between the averaged image-data information the image-data expected information with respect to the estimated age or aging range.

For example, a linear regression of the machine learning algorithm is introduced to establish the relationship between $f_t(x)$ and $g_t(x)$. Namely, the relationship $g_t(x)=a_t \times \mathrm{avg}(f_t(x))+b_t$, in which $\mathrm{avg}(f_t(x))$ is an average value of $f_t(x)$ at voxel x for all ages and aging ranges t. Through the machine learning algorithm, $a_t$ and $b_t$ can be obtained. For example, with $g_{70}(x)=a_{70} \times \mathrm{avg}(f_{70}(x))+b_{70}$, $a_{70}$ and $b_{70}$ can be obtained.

Then, in performing Step S150, based on the aforesaid relationship, the ratio and the image-data information, an estimated image-data information with respect to the estimated age or aging range can be obtained. In detail, Step S140 includes a first step of obtaining an approximate image-data expected information by plugging each of the image-data information into the relationship. For example, have $f_t(x)$ plugged into the equation at the end so as to obtain an image $g'_t(x)$ resembled to the $g_t(x)$: $g'_t(x) \approx a_t \times f_t(x)+b_t$, in which $g'_t(x)$ stands for the approximate image-data expected information. Then, based on the ratio and the approximate image-data expected information, an estimated image-data expected information with respect to the estimated age or aging range can be obtained. For example, use $r_{t/t'}(x)$ to transform $g'_t(x)$ according to $g'e(x)=g'_t(x)/r_{t/t'}(x)$, in which $g'_t(x)$ stands for the estimated image-data expected information. Then, based on the relationship and the estimated image-data expected information, the corresponding estimated image-data information can be obtained. For example, for the equation is $g'_t(x)=a_t \times \text{f-guess}_t(x)+b_t$, by giving $g'_t(x)$, $a_t$, and $b_t$, f-guess$_t(x)$ can be calculated. Herein, f-guess$_t(x)$ stands for a set of estimated image-data information for following image augmentation.

For example, if only the $f_{74}(x)$ exists in the target database, i.e., having only the nuclear-medicine brain-function image data for the age of 74, then if the image-estimated f-guess$_{70}(x)$ is wanted for the age of 70, following calculations can be performed: $g'_{74}(x) \approx a_{74} \times f_{74}(x)+b_{74}$, $g'_{70}(x)=g'_{74}(x)/r_{74/70}(x)$, and f-guess$_{70}(x)=(g'_{70}(x)-b_{70})/a_{70}$.

Then, in performing Step 160, the estimated image-data information and the image-data ratio information are linearly combined so as to generate an augmented image-data information with respect to the estimated age or aging range. In linearly combining the estimated image-data information and the image-data ratio information, following steps are included: a step of based on a first weighting value and a second weighting value to linearly combine the estimated image-data information and the image-data ratio information; and, a step of adjusting the first weighting value and the second weighting value to generate different augmented image-data information.

For example, in linearly combining the estimated image-data information and the image-data ratio information, following steps are performed. Firstly, combine f-guess$_{70}(x)$ and f-ratio$_{70}(x)$ in a weighting manner. u(x) and v(x) are adjustable per requirements, in which u(x) stands for the first weighting value, and v(x) stands for the second weighting value. Through varying u(x) and v(x), more image data can be generated. By proposing $u(x)+v(x)=1$, then f-new$_t(x)=u(x) \times \text{f-guess}_t(x)+v(x) \times \text{f-ratio}_t(x)$, in which f-new$_t(x)$ stands for the augmented image-data information. In one embodiment of this disclosure, u(x) is given by a constant 0.5, and v(x) is given also by a constant 0.5, then it can be seen as to generate a set of augmented image-data information approximating $f_{70}(x)$ according to $f_{74}(x)$.

Herein, f-new$_{70}(x)$ is not a practical or real image $f_{70}(x)$ for the same 70-year-old healthy trainee, but different f-new$_{70}(x)$ obtained by varying u(x) and v(x) according to a statistic and mathematical estimation in a Rule-Based manner. In the brain-function image data augmentation method S100 provided by this disclosure, statistic variety is achieved by introducing u(x) and v(x), so that following deep learning can be performed smoothly without being affected by possible data imbalance. Empirically, even in a situation of a shortage of ⅔ healthy trainee data, the method can still provide accurate deep learning models. In a conventional image-training session with transfer learning, at least millions or thousands of image data are required for a successful estimation. Since major cost is spent on the target database for collecting health trainee data, thus ⅔ of the cost for the target database can be saved by implementing the method provide in this disclosure.

In summary, in the brain-function image data augmentation method provided by this disclosure, the expectation-value database having given image-data expected information is introduced to expand the training data set of the deep learning.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A brain-function image data augmentation method, comprising the steps of:
   (a) providing a target database, the target database including a plurality of image-data information wherein the image data information being at least one nuclear-image brain function image data with respect to different ages;
(b) based on a plurality of image-data expected information in an expectation-value database, calculating a ratio of the plurality of image expected information with respect to the different ages;
(c) based on the plurality of image-data information and the ratio, obtaining image-data ratio information with respect to an estimated age;
(d) establishing a relationship for each pair of the image-data information and the image-data expected information;
(e) based on the relationship, the ratio and the image-data information, calculating an estimated image-data information with respect to the estimated age; and
(f) combining linearly the estimated image-data information and the image-data ratio information so as to generate an augmented image-data information with respect to the estimated age.

2. The brain-function image data augmentation method of claim 1, wherein the step (f) includes the steps of:
(f1) based on a first weighting value and a second weighting value to linearly combine the estimated image-data information and the image-data ratio information; and
(f2) adjusting the first weighting value and the second weighting value to generate different augmented image-data information.

3. The brain-function image data augmentation method of claim 1, wherein the step (b) includes a step of providing the expectation-value database, the expectation-value database including the plurality of image-data expected information, each of the plurality of image-data expected information being a mean expected image data with respect to the different ages, the mean expected image data being a voxel value greater than zero.

4. The brain-function image data augmentation method of claim 1, wherein the step (d) includes the steps of:
(d1) averaging voxel values of the plurality of image-data information to obtain an averaged image-data information; and
(d2) based on a linear regression model, establishing the relationship between the averaged image-data information and the plurality of image-data expected information with respect to the estimated age.

5. The brain-function image data augmentation method of claim 1, wherein the step (a) includes a step of capturing the nuclear-medicine brain-function image data for the different ages.

6. The brain-function image data augmentation method of claim 1, wherein the step (e) includes the steps of:
(e1) based on the relationship, obtaining an approximate image-data expected information by plugging each of the image-data information into the relationship;
(e2) based on the ratio and the approximate image-data expected information, obtaining an estimated image-data expected information with respect to the estimated age; and
(e3) based on the relationship and the estimated image-data expected information, obtaining the estimated image-data information.

* * * * *